US00PP11639P

United States Patent [19]

Mowrey et al.

[11] Patent Number: Plant 11,639

[45] Date of Patent: Nov. 21, 2000

[54] STRAWBERRY PLANT NAMED 'ALISAL'

[75] Inventors: Bruce D. Mowrey, Watsonville; JoAnne F. Coss, Salinas; Larry T. Kodama, Freedom; Joseph I. Espejo, Jr., Watsonville; Thomas M. Sjulin, Aromas, all of Calif.

[73] Assignee: Driscoll Strawberry Assoc., Inc., Watsonville, Calif.

[21] Appl. No.: 09/185,129

[22] Filed: Nov. 3, 1998

[51] Int. Cl.[7] ..... A01H 5/00

[52] U.S. Cl. ..... Plt./209

[58] Field of Search ..... Plt./209

[56] References Cited

U.S. PATENT DOCUMENTS

| | | | |
|---|---|---|---|
| P.P. 7,024 | 9/1989 | Johsno, Jr. et al. | Plt./209 |
| P.P. 8,086 | 1/1993 | Nelson et al. | Plt./209 |
| P.P. 8,649 | 3/1994 | Sjulin et al. | Plt./208 |
| P.P. 10,534 | 8/1998 | Sjulin et al. | Plt./209 |
| P.P. 11,279 | 3/2000 | Gilford et al. | Plt./209 |

*Primary Examiner*—Howard J. Locker
*Assistant Examiner*—Wendy Anne Baker
*Attorney, Agent, or Firm*—Pennie & Edmonds LLP

[57] ABSTRACT

This invention relates to a new and distinct variety of strawberry named 'Alisal'. The variety is similar to the variety 'Commander'. The variety is characterized from 'Commander', in particular, by its plant height, spread and number of crowns; bract frequency and fruit skin and flesh color.

3 Drawing Sheets

1. BACKGROUND OF THE INVENTION

The new variety orginated as a result of a controlled cross between the strawberry plant 'R2' (an unpatented variety of Driscoll Strawberry Associates, Inc.) and 'Key Largo' (U.S. Plant Pat. No. 8,649) in an ongoing breeding program, and was discovered as a seedling in a controlled breeding plot. The original seedling of the new cultivar was asexually propagated by stolons at the Driscoll Strawberry Associates, Inc. nursery in Shasta County, Calif. Propagules were transplanted to a controlled breeding plot on the Fly Ranch in Monterey County, Calif. in November of 1993 where the new cultivar first fruited in April of 1994 and was selected for further evaluation. 'Alisal' was subsequently asexually propagated and underwent further testing in the area of Watsonville, Calif. from 1995 through 1998. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Alisal'. The variety is botanically identified as *Fragaria×ananassa*. The new variety is distinguished from other varieties by a number of characteristics as set forth in Tables 1, 2 and 3.

3. COMPARISON TO CLOSEST VARIETIES

The variety which we believe to be closest to 'Alisal' from those known to us is 'Commander' (U.S. Plant Pat. No. 7,024). There are several characteristics of the new variety that are different from, or not possessed by 'Commander'. Table 1 provides information on the plant and fruit characteristics of the new variety 'Alisal' compared with characteristics of 'Commander'. Table 2 provides additional information of the plant and fruit characteristics of the new variety 'Alisal' compared with characteristics of the varieties 'Commander', 'Lido' (U.S. Plant Pat. No. 10,534), and 'Key Largo' (U.S. Plant Pat. No. 8,469). Table 3 provides isozyme characteristics of the new variety as compared to the varieties 'Commander', 'Lido' and 'Key Largo'. Data was taken from each variety as grown in a side-by-side field trial with 'Alisal'.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
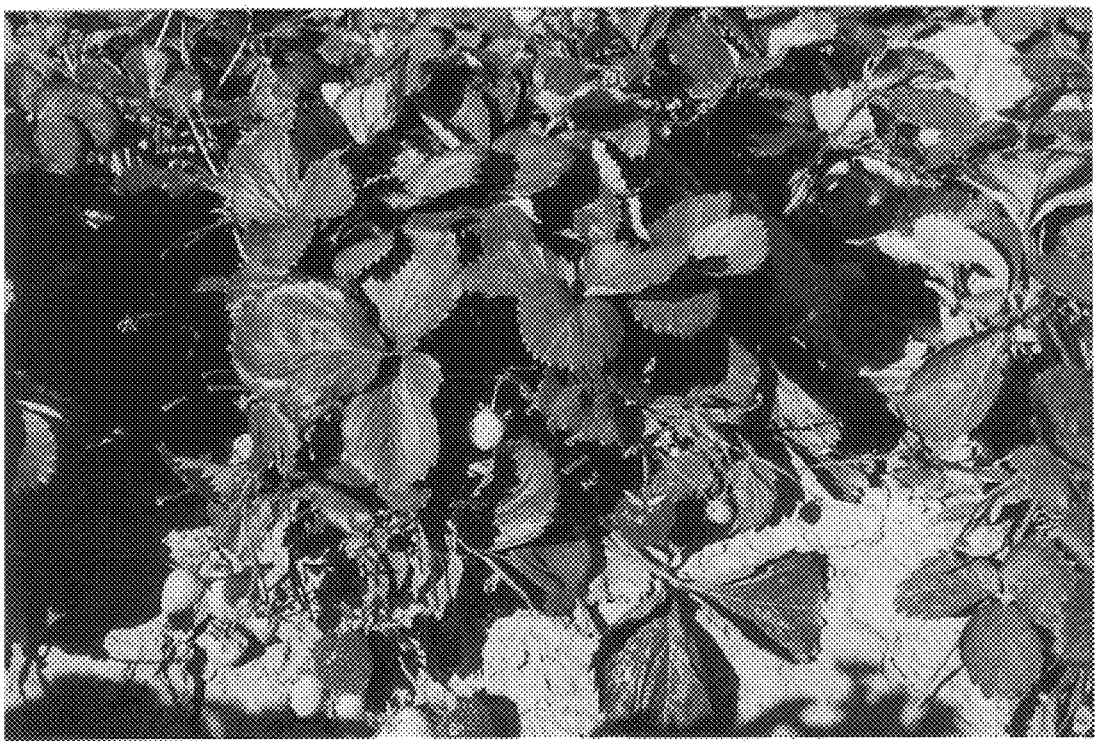
FIG. 1 shows the general characteristics of the whole plant.
Figure 2:
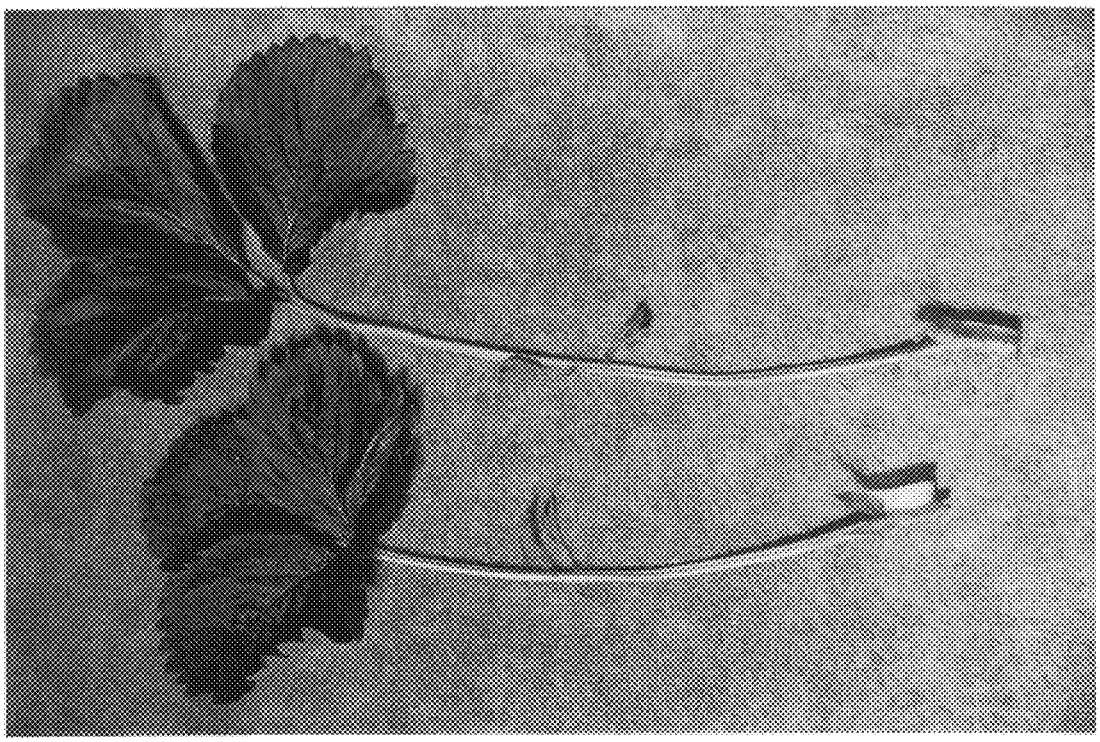
FIG. 2 shows the upper surface of two typical mature leaves of the new variety.
Figure 3:
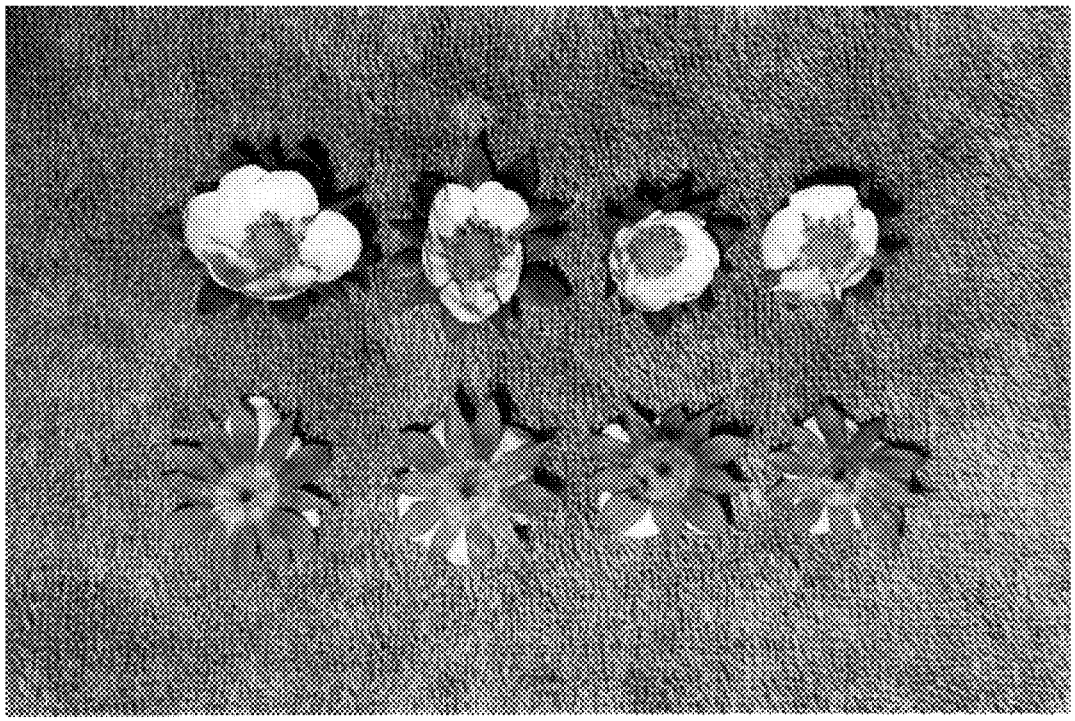
FIG. 3 shows the flower and reproductive organs of the new variety, as well as the size and position of the petals and sepals and the underside of the calyx.
Figure 4:
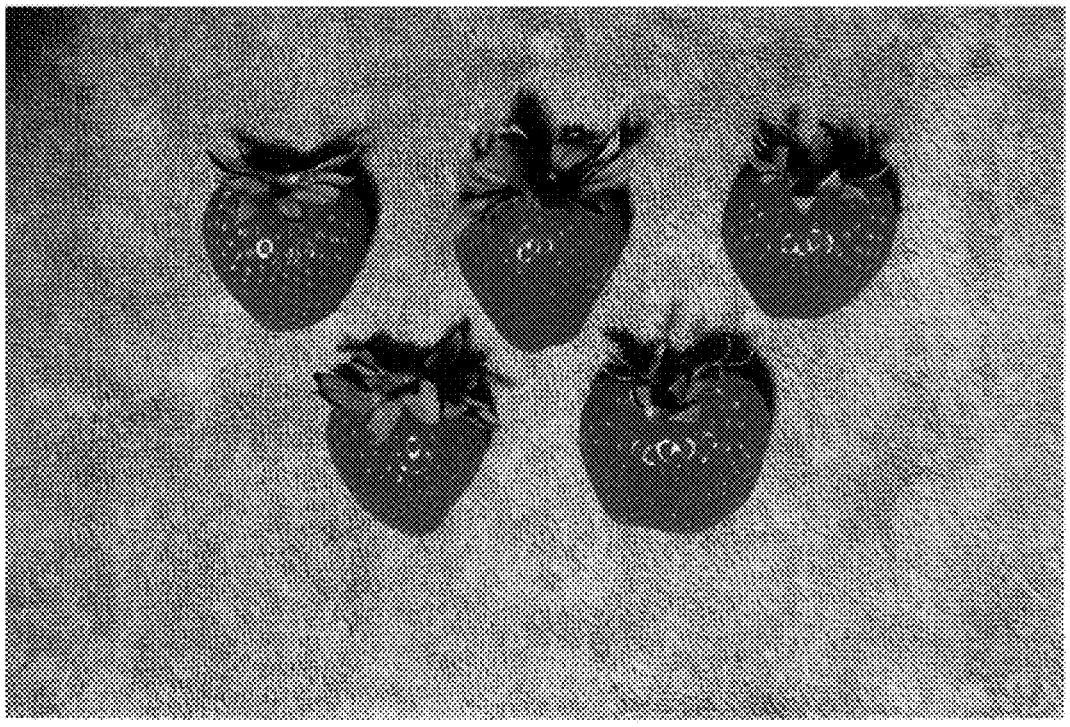
FIG. 4 shows five typical whole fruit.
Figure 5:
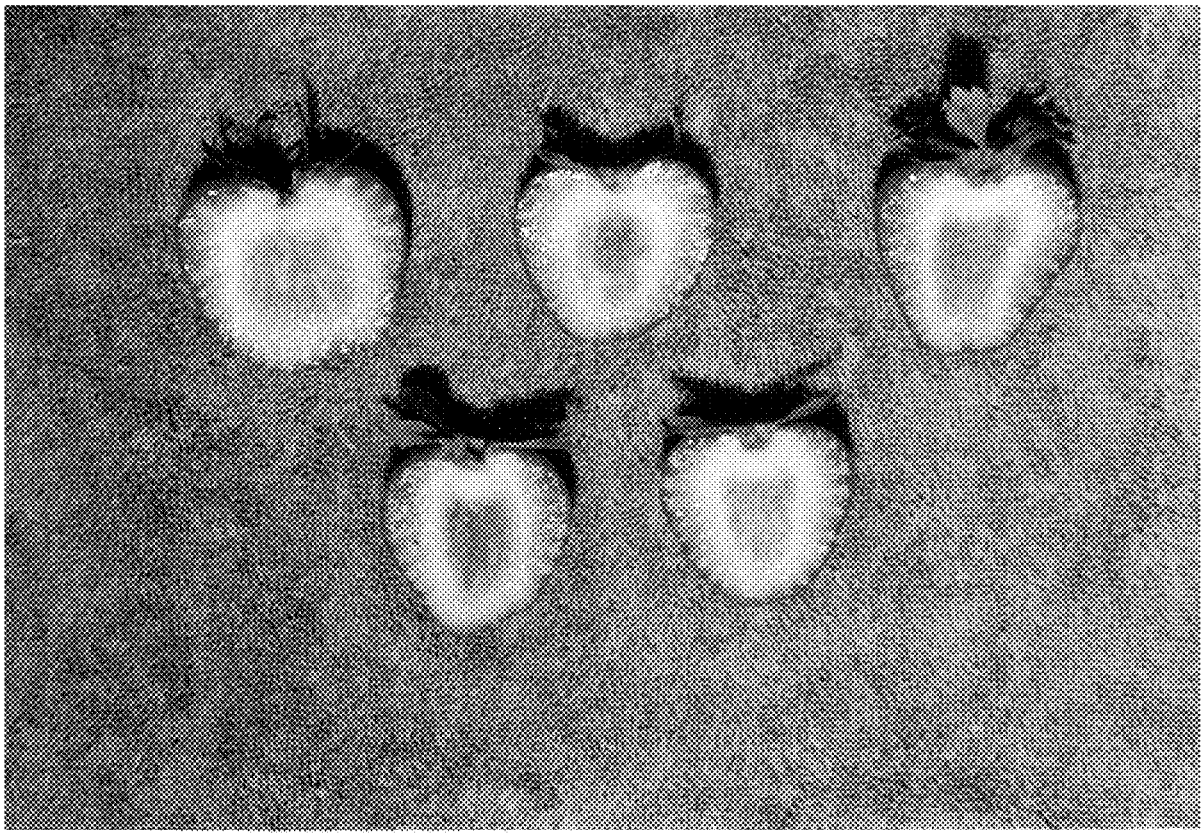
FIG. 5 shows five typical sliced fruit, illustrating the typical flesh and flesh coloration.

The following detailed description of the new variety is based upon observations taken of plants and fruit grown in Watsonville, Calif., U.S.A. Observations of 'Alisal' and 'Commander' were taken in side by side comparison in 1998. This description is in accordance with UPOV terminology. Color designations, color descriptions, and other phenotypical descriptions may deviate from the stated values and descriptions depending upon variation in environmental, seasonal, climatic and cultural conditions. Colors are described using standard Munsell Notation.

5.1 Propagation

The new variety is principally propagated by way of stolons. Although propagation by stolons is presently preferred, other known methods of propagating strawberry plants may be employed.

5.2 Characteristics of the New Variety

Information on the new variety is presented in Tables 1, 2 and 3. In the tables, the flowers described are secondary flowers except where indicated. Petal color of 'Alisal' is white (N 9.5). The fruit described is the secondary fruit on one year old plants. Fruit and flower measurements are an average of both primary and secondary fruit and flowers.

Plants and Foliage

Plants of 'Alisal' are slightly more vigorous and upright in form than those of 'Commander' in side by side trials. The foliage canopy of 'Alisal' is denser than that of 'Commander', 'Key Largo' or 'Lido' (see Table 2). The upper leaf surface of 'Alisal' is lighter green than that of 'Commander' and 'Lido' and slightly darker than that of 'Key Largo'. The shape of leaves of 'Alisal' in cross section is flatter than those of 'Commander' and 'Lido' and slightly less flat than those of 'Key Largo'. 'Alisal' has pronounced interveinal leaf blistering giving the leaves a crinkled appearance. The interveinal blistering of 'Alisal' is stronger than that of 'Commander' and much stronger than 'Lido' or 'Key Largo'. The frequency of bracts on petioles of 'Alisal' is much higher than that of 'Commander', 'Lido' or 'Key Largo'. Bracts on 'Alisal' are typically present in pairs while those on the reference cultivars are typically single. Terminal leaflets of 'Alisal' possess a higher number of teeth than those of 'Commander' and 'Key Largo' and a slightly higher number than those of 'Lido'. The leaves of 'Alisal' produce anthocyanin earlier in the fall of the year than those of 'Commander' or 'Lido'. Appearance of the anthocyanin pigment is similar in timing to that of 'Key Largo'. In 1998, leaf anthocyanin first appeared on plants of 'Key Largo' and 'Alisal' in early-October, while on plants of 'Commander' it appeared in late-October–early November.

Flower and Fruit Characteristics

The flowers of 'Alisal' are similar or slightly smaller in size than those of 'Commander', while the calyx is on average larger than that of 'Commander'. The date of first bloom for 'Alisal' ranges from early February to early April, depending on climatic conditions. The individual bloom lasts from 2 to 5 days, also depending on climatic conditions. The petals of 'Alisal' flowers are broader than long (broadly spatulate), while those of 'Commander' are as broad as thay are long. 'Alisal' typically displays 6 petals per flower, though petals may occationally number 5 or 7. The flower shape of 'Alisal' is typical of the species. 'Alisal' typically displays 10 (occasionally 12 or 14) broadly lanceolate speals. There is an average of 5.5 (range of 4 to 7) flowers per inflorescence. No fragrance is detectable. The fruit skin color of 'Alisal' is darker than that of 'Commander' and 'Lido' but similar in color to that of 'Key Largo'. The fruit flesh color of 'Alisal' is white to pale rose and is similar to that of 'Commander' and 'Lido' but lighter red than that of 'Key Largo'. The average fruit size for 'Alisal' is larger than that of 'Key Largo' but slightly smaller than that of 'Commander' and 'Lido'. The primary fruit is larger than the secondary fruit. The shape of the primary fruit is wedge to wedge-conic. The achenes of 'Alisal' are red (9.7R 2.2/5.9) to yellow (9.1YR 7.3/15.7) in color and indented. In a blind taste test, fruit of 'Alisal' has rated higher than that of 'Commander' and less than that of 'Lido'. Flavor was preferred over that of 'Commander'. The shipping ability of 'Alisal' fruit as measured by percent damaged fruit after transcontinental shipping is similar to that of 'Commander'.

The production cycle of 'Alisal' is similar to that of 'Commander' but with greater late season yield (Table 1). Production of 'Alisal' commences in early to mid-April and continues through early-November in the Watsonville, Calif. area. The chilling requirement of 'Alisal' is approximately 2 weeks of cold storage prior to planting for optional fruit yields which is intermediate to that of 'Commander' and 'Lido'. The total yield for 'Alisal' and 'Commander' are comparable when grown under similar cultural regimes.

TABLE 1

DETAILED COMPARISON OF 'ALISAL' AND 'COMMANDER'

| | Alisal | Commander |
|---|---|---|
| Plant Characteristics | | |
| Height of Plant | 22.25 cm | 20.85 cm |
| Spread of Plant | 43.95 cm | 42.80 cm |
| Number of Crowns | 6.3 | 4.1 |
| Leaf Characteristics | | |
| Terminal Leaflet Width | 8.26 cm | 7.82 cm |
| Terminal Leaflet Length | 8.38 cm | 8.06 cm |
| Terminal Leaflet Length/Width Ratio | 1.01 | 1.03 |
| Number of Teeth/Terminal Leaflet | 25.44 | 18.50 |
| Petiole Length | 22.41 cm | 20.34 cm |
| Bract Frequency | 80% | 20% |
| Stipule Length | 3.75 cm | 3.30 cm |
| Stipule Width | 0.83 cm | 1.02 cm |
| Stipule Color | 6.1GY 3.2/5.8 | 7.4GY 2.3/4.0 |
| Flower Characteristics | | |
| Petal Width | 11.8 mm | 12.7 mm |
| Petal Length | 12.5 mm | 12.5 mm |
| Petal Length/Width Ratio | 1.06 | 0.98 |
| Flower Diameter | 31.8 mm | 32.0 mm |
| Calyx Diameter | 33.2 mm | 31.3 mm |
| Fruit Characteristics | | |
| Fruit Width | 38.70 mm | 37.10 mm |
| Fruit Length | 35.40 mm | 38.00 mm |
| Fruit Length/Width Ratio | 0.91 | 1.02 |
| Average Berry Size | 22.0 g | 23.9 g |
| Fruit Skin Color | 6.6R 2.9/9.7 | 8.3R 3.5/13.0 |
| Fruit Flesh Color | 7.0R 4.3/ 16.4 & white | 9.2R 5.2/ 16.7 & white |
| Total Yield (g/plant) | 1546 | 1579 |
| Late Yield (g/plant) | 525 | 496 |

*Yield after 8/15/98

TABLE 2

CHARACTERISTICS OF 'ALISAL', 'COMMANDER', 'LIDO', and 'KEY LARGO'

| | Alisal | Commander | Lido | Key Largo |
|---|---|---|---|---|
| Plant | | | | |
| Habit | flat globose | flat globose to flat | upright to globose | globose |
| Density | medium to dense | open | open | open |
| Vigor | strong | medium | weak | weak |

TABLE 2-continued

CHARACTERISTICS OF 'ALISAL', 'COMMANDER', 'LIDO', and 'KEY LARGO'

| | Alisal | Commander | Lido | Key Largo |
|---|---|---|---|---|
| Leaf | | | | |
| Color of upper side | light green 6.1 GY 3.2/5.8 | light to medium green 8.9 GY 2.3/4.7 | medium to dark green 5.6 GY 2.3/3.6 | light green 6.1 GY 3.2/5.8 |
| Color of under side | light gray-green | light gray-green | light gray-green | light gray-green |
| Shape in cross section | siightly concave to flat (mostly flat) | concave | concave | flat |
| Interveinal blistering | strong to very strong | medium to strong | medium | medium |
| Glossiness | weak to medium | medium to strong | weak to medium | medium |
| Number of leaflets | 3 | 3 | 3 | 3 |
| Terminal leaflet margin profile | revolute to flat | revolute to flat | flat | revolute to fiat |
| Terminal leaflet length/width ratio | 1.01 | 1.03 | 1.00 | 1.03 |
| Terminal leaflet shape of base | acute to obtuse | obtuse | obtuse | acute to obtuse |
| Terminal leaflet shape of teeth | obtuse | obtuse to rounded | rounded | acute |
| Terminal leaflet average number of teeth | 25.4 | 18.5 | 22.6 | 19.7 |
| Petiole pubescence | very sparse to sparse | sparse | sparse to medium | sparse to medium |
| Petiole pose of hairs | outwards | outwards | upwards to outwards | upwards |
| Bracts frequency on petioles | 80% (mostly double) | 20% (mostly single) | 50% (mostly single) | 10% (mostly single) |
| Stolon | | | | |
| Number | many | medium to many | few to medium | few to medium |
| Anthocyanin coloration | strong | weak to medium | medium | medium to strong |
| Thickness | medium | medium | thick | thin |
| Pubescence | medium to dense | sparse | medium to dense | sparse |
| Inflorescence | | | | |
| Position relative to foliage | above | level to above | level to above | above |
| Flower size | medium to large | large | medium | small to medium |
| Diameter of calyx relative to corolla | larger to same size | same size to larger | same size | larger to much larger |
| Diameter of inner calyx relative to outer | smaller to same size | same size | larger | larger |
| Spacing of petals | over-lapping | over-lapping | over-lapping | over-lapping |
| Petal length/width ratio | longer than broad | broader than long to as long as broad | broader than long | as long as broad |

TABLE 2-continued

CHARACTERISTICS OF 'ALISAL', 'COMMANDER', 'LIDO', and 'KEY LARGO'

| | Alisal | Commander | Lido | Key Largo |
|---|---|---|---|---|
| Fruiting Truss | | | | |
| Attitude at first picking | semi-erect | prostrate | erect to semi-erect | semi-erect to prostrate |
| Length | medium to long | medium | short to medium | long |
| Fruit | | | | |
| Length/Width Ratio | broader than long to as long as broad | as long as broad | as long as broad | as long as broad to longer than broad |
| Weight | 22.0 g | 23.9 g | 24.2 g | 20.3 g |
| Predominant shape | conical to cordate | conical to bi-conical | cordate | conical |
| Difference in shapes between primary and secondary fruits | moderate to marked | slight | moderate to marked | slight |
| Band without achenes | very narrow to narrow | narrow to medium | absent or very narrow | absent or very narrow |
| Unevenness of surface | weak | weak | medium | very weak to weak |
| Skin color | red to dark red 6.6R 2.9/9.7 | orange red 8.3R 3.5/13.0 | red 6.6R 3.2/12.6 | red 5.5R 2.9/11.6 |
| Evenness of color | even | slightly uneven | even | even |
| Glossiness | strong | strong | strong | weak to medium |
| Insertion of achenes | below the surface | level with the surface | below to level with the surface | below to level with the surface |
| Insertion of calyx | in a basin | level | in a basin | level |
| Pose of the calyx segments | spreading to reflex | spreading | spreading to reflex | spreadirig to reflex |
| Size of calyx in relation to fruit | same size | same size | smaller | same size to larger |
| Firmness of flesh | soft to medium | medium | medium to firm | medium to firm |
| Color of flesh | white to pale rose and white 7.0R 4.3/16.4 | light red to orange red 9.2R 5.2/16.7 | pale rose & white 7.8 R/ 5.2/16.5 | orange red 6.8R 3.7/15.8 |
| Evenness of flesh color | uneven | slightly uneven | slightly uneven | slightly uneven |
| Distribution of flesh color | only marginal | marginal and central | marginal and central | marginal and central |
| Hollow center size | small | medium | absent | small to medium |
| Sweetness | medium to strong | medium to strong | strong | medium |
| Texture when tasted | fine to medium | fine to medium | fine | medium |
| Acidity | weak | weak to medium | weak | medium |

5.3 Resistance to Stress

The new variety is moderately resistant to high soil pH and moderately susceptible to high soil salt levels.

5.4 Insect and Disease Resistance and Susceptibility

The 'Alisal' variety is moderately susceptible to *Xanthomonas fragariae* and Botrytis fruit rot. The variety is moderately resistant to Powdery Mildew. 'Alisal' is susceptible to Verticillium wilt. The 'Alisal' variety is also susceptible to injury by the two-spotted spider mite (*Tetranychus urticae*) and lygus bug (*Lygus hesperus*).

5.5 ISOZYME ANALYSIS

In addition to the morphological description above, the new cultivar 'Alisal' has been analyzed to obtain an indication of its genetic makeup to provide further means for identifying the new variety and distinguishing it from some other somewhat similar and/or relates strawberry varieties. Specifically, leaf samples of 'Alisal', 'Commander', 'Lido' and 'Key Largo' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme characterization of the three varieties is presented in Table 3, with the letters representing the banding patterns for each enzyme as designated in the above-identified article.

TABLE 3

ISOZYME PHENOTYPES FOR 'ALISAL', 'COMMANDER', 'LIDO' AND 'KEY LARGO'

| Locus | Alisal | Commander | Lido | Key Largo |
|---|---|---|---|---|
| PGI | A4 | A4 | A3 | A1 |
| LAP | B3 | B3 | B3 | B3 |
| PGM | C4 | C4 | C2 | C4 |

/

What is claimed is:

1. A new and distinct variety of strawberry plant, substantially as shown and described.

* * * * *